United States Patent [19]

Holcombe

[11] 4,210,771

[45] Jul. 1, 1980

[54] TOTAL ISOMERIZATION PROCESS

[75] Inventor: Thomas C. Holcombe, Scarsdale, N.Y.

[73] Assignee: Union Carbide Corporation, New York, N.Y.

[21] Appl. No.: 957,288

[22] Filed: Nov. 2, 1978

[51] Int. Cl.² .............................................. C07C 5/30
[52] U.S. Cl. .................................... 585/701; 585/738; 585/739; 585/822; 585/823
[58] Field of Search ...................... 260/683.65, 683.73; 208/91, 85; 585/701, 738, 739

[56] References Cited

U.S. PATENT DOCUMENTS

| | | | |
|---|---|---|---|
| 2,886,509 | 5/1959 | Christensen et al. | 208/91 |
| 2,909,583 | 10/1959 | Bleich | 260/683.73 |
| 2,921,104 | 1/1960 | Haensel | 260/683.65 |
| 3,069,349 | 12/1962 | Meiners | 208/85 |

*Primary Examiner*—George Crasanakis
*Attorney, Agent, or Firm*—Dominic J. Terminello

[57] ABSTRACT

A process for virtually complete isomerization of the normal paraffin hydrocarbons contained in a feed stream consisting essentially of mixed normal and non-normal hydrocarbons, wherein the feedstock is first passed through an isomerization reactor and the hydrocarbons in the effluent from the reactor are passed through an adsorption section wherein the normals are adsorbed and the non-normals passed out of the system as an isomerate product. The fresh feed is controllably flow blended with the variable desorption effluent from the adsorber beds containing desorption normals and hydrogen purge gas in order to provide a constant flow of combined feed to the isomerization reactor.

5 Claims, 1 Drawing Figure

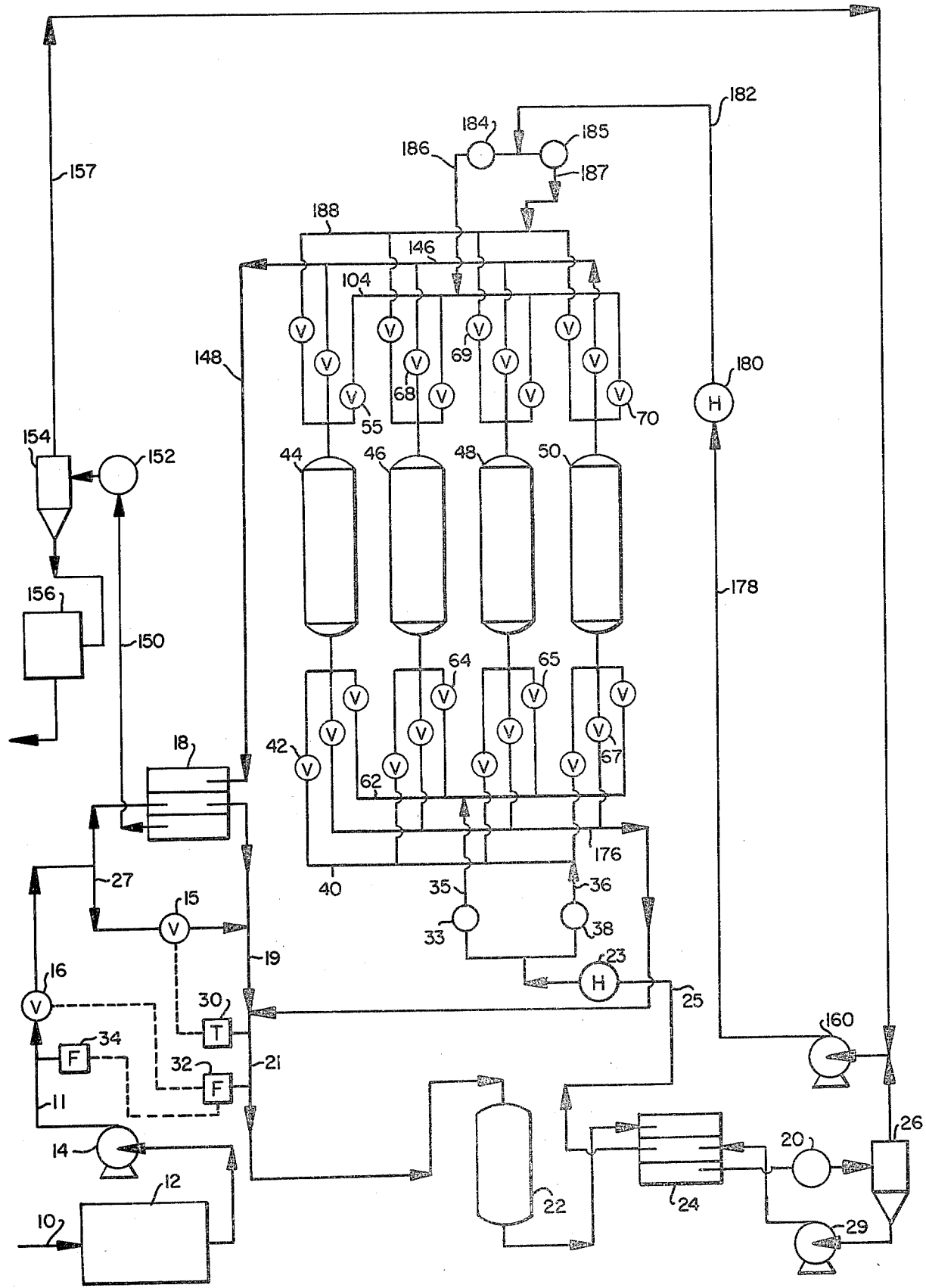

TOTAL ISOMERIZATION PROCESS

This invention relates to a process for improving the octane rating of certain petroleum fractions by virtually complete isomerization of the normal paraffin hydrocarbons contained in a feed stream essentially of mixed normal and non-normal hydrocarbons. More particularly, this invention relates to virtually complete isomerization of normal pentanes and normal hexanes contained in a feed stream containing normal pentanes and normal hexanes, as well as non-normal hydrocarbons to form branched chain iso/pentanes and iso/hexanes. This process will be referred to hereinafter, from time to time, as the total isomerization process or TIP.

Essentially, the present process comprises passing a stream containing a mixture of normal and non-normal hydrocarbons into an isomerization reactor to catalytically isomerize at least a portion of the normals in the presence of hydrogen by contact in the reactor with a catalyst composition, which preferably is a zeolitic molecular sieve with a hydrogenation component. Other catalyst compositions such as alumina-base catalysts may be used as well. The temperature of the reactor is dependent in part on the particular catalyst employed, but preferably is within the range of 200° C. to 390° C. and the pressure in the reactor ranges between 175 psia and 600 psia when a molecular sieve catalyst is employed. The effluent from the reactor still contains approximately 20-30 wt-% normals. The hydrocarbon fraction of the reactor effluent stream is circulated to a zeolitic molecular sieve adsorbent bed where the normals are selectively adsorbed and the non-normals are passed out of the adsorber as an adsorber effluent and eventually an isomerate product. The normals are then desorbed from the bed using a hydrogen purge stream. The fresh feed is controllably flow mixed with the variable desorption effluent containing normals and hydrogen purge gas, and then introduced into the reactor where the isomerization reaction takes place.

This invention is predicated on the discovery of a process wherein fresh feed to the system is flow blended at varying flow rates with the variable desorption effluent from the iso/normal separation adsorbers, in order to provide a more uniform combined feed to the isomerization reactor.

The adsorption section of the present invention includes typical state-of-the art adsorption systems. In this regard the mixed normal and non-normal hydrocarbon stream introduced from the reactor to the adsorbers is introduced at a temperature and pressure similar to that of the reactor, namely 200° C. to 390° C. and 175 to 600 psia. The adsorbers contain an adsorbent capable of selectively adsorbing normal paraffins and excluding branched chain paraffins. The normal paraffins are desorbed from the adsorbent bed with a countercurrent hydrogen purge stream. The desorbed normals and the hydrogen purge gas is then passed to the isomerization reactor.

In the prior art the hydrogen purge gas is recycled and flow controlled to the adsorbers. As the hydrogen passes countercurrently through the adsorbent bed, normals are gradually desorbed and pass into the desorption effluent at a varying rate. The normals concentration in the desorption effluent typically varies from 20 to 30 mole percent at the beginning of the step to less than 5 mole percent at the end of the step. Fresh feed is pumped, flow controlled, partially heated and then blended with the desorption effluent prior to introduction into the reactor. The colder fresh feed stream quenches the desorption effluent to provide a combined lower temperature stream to the reactor. A temperature control on the combined reactor feed adjusts the fresh feed bypass around a heat exchanger thereby varying the degree of feed preheat and thus providing the quenching duty required. As is known in the art, a minimum hydrogen partial pressure is required in the reactor to minimize coking of the catalyst which is deleterious to catalyst life. The minimum hydrogen partial pressure required is dependent on the catalyst used, but usually is in the range of 100-250 psia.

The partial pressure of the hydrogen is a function of the hydrogen concentration in the combined reactor feed. With a varying flow rate of desorbed normals and a constant flow rate of fresh feed, the recycled hydrogen flow must be added at a sufficient rate to insure that a minimum partial pressure is maintained at the worst case, which is when the desorbed normals are at maximum flow rate. Accordingly, in the prior art the system is designed to provide hydrogen flow rate for the worst case, which means there is more than enough hydrogen present as the desorbed normals flow rate decreases from maximum to minimum. This means that the mass flow rate of the combined reactor feed (hydrogen and desorbed normals plus fresh feed) varies considerably from maximum to minimum due to the fluctuations in the desorbed normals flow rate. This large fluctuation causes major variations in pressure drops and cooling requirements in the reactor and downstream equipment.

In the present invention, the fresh feed rate is constantly monitored and varied to provide a constant flow rate of combined reactor feed. In one embodiment of the invention, a flow controller at the reactor inlet directly adjusts the fresh feed control valve. A range control instrument monitors the flow rate of the fresh feed, computes average flow rates and adjusts the set point on the combined reactor feed flow controller to provide the desired average fresh feed flow rate. Since the rate of recycle hydrogen in this desorption effluent and combined reactor feed is constant, and also since the molecular weight of the fresh feed and desorbed normals are essentially the same, this system varies the fresh feed in an inverse relationship with the desorbed normals rate and assures a constant flow rate of hydrocarbons to the reactor. Since the fluctuations in hydrocarbon flow rates are eliminated, the recycle hydrogen flow rate required to provide a minimum hydrogen partial pressure in the reactor is reduced. Thus, this invention allows a substantial reduction in recycle hydrogen rate. Also, this invention permits a substantial improvement in the heat integration by taking full advantage of the fact that when minimum heat is available in the adsorption effluent, minimum heat is required by the variable fresh feed. Likewise, when the variable fresh feed requires maximum heat, maximum heat is available in the adsorption effluent.

Since this invention reduces the combined reactor feed flow rate, the catalyst volume is reduced, while still providing the same catalyst residence time and isomerization performance. Furthermore, the mass flow rate of the combined reactor feed is virtually constant for the present invention. Thus, the fluctuations in pressure drops and cooling requirements associated with the previous state-of-the-art are eliminated. The required oversizing of the downstream cooling and compression equipment are also eliminated.

Accordingly, it is an object of this invention to provide a TIP process wherein more uniform flow rates and compositions of the combined feed are provided to an isomerization reactor.

Another object is to reduce the recycle hydrogen flow rate in a TIP process while maintaining a minimum partial pressure over the isomerization catalyst to ensure long catalyst life.

Still another object is to provide a TIP process which has improved heat integration.

Yet another object is to stabilize the pressure drops and cooling requirements in the isomerization reactor and downstream equipment.

These and other objects will either be pointed out or become apparent from the following description and drawings wherein the sole FIGURE is a flow scheme of a typical system for practicing the present invention.

In a broad aspect the invention provides an integrated TIP process for improving the octane rating of a mixed hydrocarbon feedstock containing saturated paraffins having from 5 to 6 carbon atoms, which comprises passing said feedstock through an isomerization reactor containing a catalyst composition and a hydrogenation component in the presence of hydrogen to convert at least a portion of the normal hydrocarbons in the feedstock to non-normals; the hydrocarbons in the effluent from the reactor are passed to the adsorption section of the system where the normals are adsorbed in a molecular sieve zeolite adsorber bed and the non-normals are eventually passed out of the system as an isomerate product. The adsorber beds, after the adsorption cycle, are desorbed by a hydrogen purge gas producing a desorption vapor effluent containing desorbed normals and hydrogen purge gas. Fresh feed is blended with the desorption effluent at varying feed rates to provide a constant flow rate of combined reactor feed (hydrogen plus desorbed normals plus fresh feed) to the reactor.

In a more limited aspect of this invention, the fresh feed blending with the desorption effluent is accomplished in one embodiment by monitoring the flow to the isomerization reactor by a flow control device, and varying the fresh feed flow rate in response to variation in flow of the combined reactor feed and monitoring the flow rate of fresh feed by a range control instrument which computes average fresh feed flow rates and automatically compares the actual average flow with the desired average flow present and adjusts, in response thereto, the set point on the combined fresh feed flow controller to provide the desired average fresh feed flow rate and keep the combined reactor feed rate essentially constant.

The feedstock to the reactor is composed principally of the various isomeric forms of saturated hydrocarbons having from 5 to 6 carbon atoms inclusive. Such feedstocks are normally the result of refinery distillation operations, and thus may contain small amounts of $C_7$ and even higher hydrocarbons, but these are frequently present, if at all, only in trace amounts. Olefinic hydrocarbons are advantageously less than about 4 mole percent in the feedstock. Aromatic and cycloparaffin molecules have a relatively high octane number, but are to a substantial degree cracked and/or converted into molecules of much lower octane number in the isomerization reactor. Accordingly, the preferred feedstock should not contain more than about 25 mole percent combined aromatic and cycloparaffinic hydrocarbons. Advantageously, the $C_5$ and $C_6$ non-cyclic paraffins comprise at least 75 mole percent of the feedstock, with at least 25 mole percent being normal pentane and/or normal hexane. A feedstock of the following composition is typical:

| Components | Weight-% |
|---|---|
| $C_4$ minus | 4.1 |
| i-$C_5$ | 24.5 |
| n-$C_5$ | 27.8 |
| i-$C_6$ | 27.4 |
| n-$C_6$ | 14.7 |
| $C_7$ plus | 1.5 |

In the foregoing description of the feedstocks suitably treated in accordance with the present process the expression "the various isomeric forms of pentane and hexane" is intended to denote all the branched chain and cyclic forms of the compounds, as well as the straight chain forms. Also, the prefix notations "iso" and "i" are intended to be generic designations of all branched chain and cyclic forms of the indicated compound.

The hydrogen stream used as the purge gas in desorbing the adsorption bed and as the hydrogenation material in the isomerization reactor need not be pure and is generally composed of one or a combination of two or more refinery hydrogen streams such as reformer hydrogen and the like. Any impurities present should be relatively non-sorbable and inert toward the zeolite adsorbent, the zeolite catalyst and the hydrocarbons in the system. It will be understood that light hydrocarbons containing from 1 to 4 carbon atoms inclusive will appear in the recycle hydrogen in the course of operation of the process since these low boiling materials are produced in the catalytic unit. Preferably, the recycle hydrogen stream is at least 50 mole percent hydrogen.

The zeolitic molecular sieve employed in the adsorption bed must be capable of selectively adsorbing the normal paraffins of the feedstock using molecular size and configuration as the criterion. Such a molecular sieve should, therefore, have an apparent pore diameter of less than about 6 Angstroms and greater than about 4 Angstroms. A particularly suitable zeolite of this type is zeolite A, described in U.S. Pat. No. 2,883,243, which in several of its divalent exchanged forms, notably the calcium cation form, has an apparent pore diameter of about 5 Angstroms, and has a very large capacity for adsorbing normal paraffins. Other suitable molecular sieves include zeolite R, U.S. Pat. Nos. 3,030,181; zeolite T, 2,950,952, and the naturally occurring zeolitic molecular sieves chabazite and erionite. The term "apparent pore diameter" as used herein may be defined as the maximum critical dimension, or the molecular species which is adsorbed by the adsorbent under normal conditions. The critical dimension is defined as the diameter of the smallest cylinder which will accommodate a model of the molecule constructed using the available values of bond distances, bond angles and van der Waals' radii. The apparent pore diameter will always be larger than the structural pore diameter, which can be defined as the free diameter of the appropriate silicate ring in the structure of the adsorbent.

The zeolitic catalyst preferably used in the isomerization reactor can be any of the various molecular sieve based catalyst compositions well known in the art which exhibits selective and substantial isomerization activity under the operating conditions of the present process. As a general class, such catalysts comprise the crystalline zeolitic molecular sieves having an apparent pore diameter large enough to adsorb neopentane, a $SiO_2/Al_2O_3$ molar ratio of greater than 3; less than 60, preferably less than 15, equivalent percent alkali metal cations and having those $AlO_4^-$ tetrahedra not associated with alkali metal cations either not associated with any metal cation, or associated with divalent or other polyvalent metal cations, said zeolitic component being combined with a hydrogenation catalyst, preferably a noble metal of group VIII of the Periodic classification of the Elements. The catalyst composition can be used alone or can be combined with a porous inorganic oxide diluent as a binder material. The hydrogenation agent can be carried either on the zeolitic component and/or on the binder. A wide variety of inorganic oxide diluent materials are known in the art—some of which exhibit hydrogenation activity per se. It will, accordingly, be understood that the expression "an inorganic diluent having a hydrogenation agent thereon" is meant to include both diluents which have no hydrogenation activity per se and carry a separate hydrogenation agent and those diluents which are per se hydrogenation catalysts. Oxides suitable as diluents, which of themselves exhibit hydrogenation activity, are the oxides of the metals of Group VI of the Mendeleev Periodic Table of Elements. Representative of these metals are chromium, molybdenum and tungsten. It is preferred, however, that the diluent material possess no pronounced catalytic activity per se, especially cracking activity. In all events, the diluent should not exhibit a greater quantitative degree of cracking activity than the zeolitic component of the overall isomerization catalyst composition. Suitable oxides of this latter class are the aluminas, silicas, the oxides of metals of Groups III, IV-A and IV-B of the Mendeleev Periodic Table, and cogels of silica and oxides of the metals of the Groups III, IV-A and IV-B, especially alumina, zirconia, titania, thoria and combinations thereof. Aluminosilicate clays such as kaolin, attapulgite, sepiolite, polygarskite, bentonite, montmorillonite and the like when rendered in a pliant plastic-like condition by intimate admixture with water are also suitable diluent materials, particularly when said clays have not been acid-washed to remove substantial quantities of alumina. Superior catalysts for isomerization reactions are disclosed in detail in U.S. Pat. Nos. 3,236,761 and 3,236,762. A particularly preferred catalyst is one prepared from a zeolite Y (U.S. Pat. No. 3,130,007) having a $SiO_2/Al_2O_3$ molar ratio of about 5 by reducing the sodium cation content to less than about 15 equivalent percent by ammonium cation exchange, then introducing between about 35 and 50 equivalent percent of rare earth metal cations by ion exchange and thereafter calcining the zeolite to effect substantial deammination. As a hydrogenation component, platinum or palladium in an amount of about 0.1 to 1.0 weight percent can be placed on the zeolite by any conventional method.

Depending on the particular catalyst composition employed, the operating temperature of the isomerization reactor is generally within the range of 200° C. to 390° C. and the pressure is within the range of 175 to 600 psia. Although it is preferable to carry out the overall adsorption separation and isomerization process under essentially isobaric and isothermal conditions, the effective operating conditions in the adsorption beds are somewhat broader in range than in the isomerizer. Pressures above atmospheric in conjunction with temperatures in the range of 200° C. to 390° C. which maintain the feedstock in the vapor state are suitable for operation of the adsorbers.

"Bed void space" for purposes of this invention is intended to mean any space in the bed not occupied by solid material except the intracrystalline cavities of the zeolite crystals. The pores within any binder material which may be used to form agglomerates of the zeolite crystals is considered to be bed void space.

In a preferred embodiment of the present invention, as described in U.S. Pat. No. 3,700,589, issued Oct. 24, 1972, the hydrocarbons in the effluent from the isomerization reactor are passed as feed in the vapor state and at superatmospheric pressure periodically in sequence through each of at least four fixed beds of a system containing a zeolitic molecular sieve adsorbent having effective pore diameters of substantially 5 Angstroms, each of said beds cyclically undergoing the stages of:

A-1 adsorption-fill, wherein the vapor in the bed void space consists principally of a non-sorbable purge gas and the incoming feedstock forces the said non-sorbable purge gas from the bed void space out of the bed without substantial intermixing thereof with non-adsorbed feedstock fraction;

A-2 adsorption, wherein the feedstock is cocurrently passed through said bed and the normal constituents of the feedstock are selectively adsorbed into the internal cavities of the crystalline zeolitic adsorbent and the nonadsorbed constituents of the feedstock are removed from the bed as an effluent having a greatly reduced content of non-feedstock constituents;

D-1 void space purging, wherein the bed loaded with normals adsorbate to the extent that the stoichiometric point of the mass transfer zone thereof has passed between 85 and 97 percent of the length of the bed and containing in the bed void space a mixture of normals and non-normals in essentially feedstock proportions, is purged countercurrently, with respect to the direction of A-2 adsorption by passing through the bed a stream of a non-sorbable purge gas in sufficient quantity to remove said void space feedstock vapors but not more than that which produces about 50 mole percent, preferably not more than 40 mole percent, of adsorbed feedstock normals in the bed effluent; and D-2 purge desorption, wherein the selectively adsorbed feedstock normals are desorbed as part of the desorption effluent by passing a non-sorbable purge gas countercurrently with respect to A-2 adsorption through the bed until the major proportion of adsorbed normals has been desorbed and the bed void space vapors consist principally of non-sorbable purge gas.

This invention can also be practiced with any multiple bed adsorption system, i.e. the three bed adsorption system, as described in U.S. Pat. No. 3,770,621, issued Nov. 6, 1973.

For purpose of illustrating the invention the following description and example is provided in conjunction with the drawing. For purposes of exemplification, the composition of the fresh feed may be 4.1 mole percent $C_1$ to $C_4$; 52.3 mole percent $C_5$; and 43.6 mole percent $C_6$. With reference to the drawings, fresh feed is fed through line 10 to accumulator tank 12 from which it is drawn by pump 14 through control valve 16. The fresh feed may then pass to heat exchanger 18 where it is partially heated by heat exchange with effluent from an adsorption bed undergoing A-2 adsorption. The partially heated fresh feed from exchanger 18 passes through lines 19 to line 21 where it combines with desorption effluent from an adsorption bed undergoing D-2 desorption at 650° F. to provide a combined reactor feed temperature of about 550° F. The combined reactor feed flow rate is 6,537 lb. moles/hr. The reactor feed is passed to isomerization reactor 22. The catalyst in the reactor is zeolite Y-palladium composition in which the zeolite has a molar $SiO_2/Al_2O_3$ molar ratio of 5; a sodium cation for operation of about 10 equivalent percent and a rare earth cation population of about 43 equivalent percent. The composition contains 0.5 wt-% finely divided palladium. The effluent from the reactor 22 flows through heat exchanger 24 and water cooler 20 to separator 26. The adsorber feed is drawn from separator 26 by pump 29 and passes through exchanger 24 and line 25 to heater 23 where it is heated to 650° F. before passing to the separation section of the system.

In this invention there is provided a bypass line 27 around heat exchanger 18. Also provided in line 21 is a temperature controller 30 which adjusts control valve 15 to bypass fresh feed around the exchanger 18 and to control the heat added to the fresh feed. In addition, in line 21 there is a flow controller 32 which monitors the total combined reactor feed and which in turn operates control valve 16 to provide varying flow of fresh feed. A range control instrument 34 is located in line 11 between pump 14 and control valve 16 and monitors the flow rate of the fresh feed, computes average flow rates, compares the average to a point set on the instrument, and adjusts the set point on the combined reactor feed controller 32 to provide the desired average fresh feed flow rate. Assuming the recycle hydrogen flow rate is 5,107 lb. moles/hr. and since it is constant in the desorption effluent, this system varies fresh feed in an inverse relationship with desorbed normals flow rate and assures a constant flow rate of hydrocarbons to the reactor 22.

The separation portion of the system is prior art technology and operates as follows:

Adsorber feed from line 25 and exchanger 24 is directed partially to line 35 by way of pressure control valve 33 and partially to line 36 by means of flow rate control valve 38. Through line 36 a portion of the feed from line 25, averaging 676 lb. moles/hr., is directed through manifold 40 and valve 42 to adsorption bed 44 undergoing A-1 adsorption. Each of the four adsorption beds in the system, namely beds 44, 46, 48 and 50 contain 72,500 pounds of calcium zeolite A in the form of 1/16 inch cylindrical pellets. Each bed is 15 feet long and 12 feet in diameter. Bed 44, at the time that feed passing through valve 42 enters, contains residual hydrogen purge gas from the preceding desorption stroke. The rate of flow of the feed through line 36, manifold 40 and valve 42 is controlled such that bed 44 is flushed of residual hydrogen uniformly over a period of about two minutes, i.e. the effluent from bed 44 exits at an average rate of about 585 lb. moles/hr. During this first stage of adsorption in bed 44, the hydrogen effluent passes from the bed through valve 55 into manifold 104. During the two minute period when the hydrogen was being flushed from bed 44, the remaining feed passes through valve 33 and line 35, through manifold 62, and valve 64 to bed 46, at the average rate of 1028 lb. moles/hr. The normal paraffins in the feed are adsorbed by bed 46 undergoing A-2 adsorption and the non-adsorbed non-normals emerge from the bed through valve 68 and are fed to manifold 146. The non-normals flow through line 148, heat exchanger 18, line 150, water cooler 152, separator 154 and the condensed product is accumulated in accumulator 156. The residual hydrogen purge gas in the non-normals effluent leaves separator 154 through 157, to purge recycle compressor 160. During the two minute period when the residual hydrogen is being flushed from bed 44, i.e. A-1 adsorption, bed 48 is undergoing the first stage of purging with hydrogen wherein the hydrocarbons in the bed void space are being flushed from the bed, i.e. D-1 purging. During the same two minute interval, bed 50 is undergoing the second stage of desorption, i.e. D-2 purge desorption, in which the normal hydrocarbons are desorbed from the molecular sieve adsorbent using hydrogen and removed from the bed. From compressor 160, the hydrogen purge gas stream is passed through line 178 and heater 180, wherein it is heated to about 650° F., and thence through line 182. By means of flow control valves 184 and 185 the gas flow from line 182 is divided into two streams, the lesser stream being passed at the average rate of 580 lb. moles/hr. through line 187, manifold 188, and valve 69 counter-currently (with respect to the previous adsorption stroke) through bed 48. The low controlled flow rate employed for the two minute first stage desorption is for the purpose of flushing non-adsorbed hydrocarbons from the bed voids without causing excessive desorption of the normals from the adsorbent. The effluent from bed 48, at an average flow rate of 770 lb. moles/hr., passes through valve 65 and into manifold 62 where it is recycled through valve 64 directly to bed 46 undergoing A-2 adsorption. The major portion of the hydrogen stream from line 182, averaging 4,820 lb. moles/hr., is passed through control valve 184, line 186, to manifold 104 where it is mixed with the previously mentioned first stage adsorption effluent from valve 55 and then passes through valve 70 and bed 50. During this period, selectively adsorbed normal paraffins are desorbed from the zeolitic molecular sieve and flushed from the bed. The effluent from bed 50 consisting of 5,107 lb. moles/hr. of recycled hydrogen and an average desorbed normal paraffins rate of 400 lb. moles/hr. passes through valve 67 and manifold 176 to line 21, where it is mixed with incoming fresh feed.

The foregoing description is for a single two minute period of a total eight minute cycle for the system. For the next two minute period, appropriate valves are operated so that bed 44 begins A-2 adsorption, bed 46 begins D-1 purging, bed 48 begins D-2 desorption, and bed 50 begins A-1 adsorption. Similarly, a new cycle begins after each two minute period and at the end of an eight minute period all the beds have gone through all stages of adsorption and desorption.

The following chart indicates the functioning of each of the four beds for each two minute period:

| TIME, min. | 0-2 | 2-4 | 4-6 | 6-8 |
|---|---|---|---|---|
| Bed 44 | A-1 | A-2 | D-1 | D-2 |
| Bed 46 | A-2 | D-1 | D-2 | A-1 |
| Bed 48 | D-1 | D-2 | A-1 | A-2 |
| Bed 50 | D-2 | A-1 | A-2 | D-1 |

In the foregoing embodiment of the invention, the desorption effluent composition and required fresh feed rates vary during each two minute period. At the beginning of the two minute period, when a new bed begins D-2 desorption, the average molecular weight and specific heat of the D-2 effluent is at its maximum. Conversely, at the end of the two minute period, the average molecular weight and specific heat of the D-2 effluent is at its minimum. Since one function of the variable fresh feed is to quench the desorption effluent from about 650° F. to about 550° F., the quantity of heat exchanged to the fresh feed in heat exchanger 18 varies from a minimum at the beginning of the two minute period to a maximum at the end of the two minute period. The adsorption effluent, which is used to preheat the fresh feed in heat exchanger 18, also has a varying average molecular weight, which results from the entrained hydrogen leaving in the non-normal hydrocarbons at varying rates. In particular, at the beginning of the two minute period, when a new bed begins A-2 adsorption, the entrained hydrogen concentration of the effluent is at its maximum. Conversely, at the end of the two minute period, the hydrogen concentration in the effluent is at its minimum. Therefore, the available heat in the adsorption effluent varies from a minimum at the beginning of the two minute period to a maximum at the end of the two minute period. By heat exchanging the fresh feed directly with the adsorption effluent in heat exchanger 18, the fresh feed heating requirements vary in unison with the available heat in the adsorption effluent during the two minute period and improved heat integration is accomplished.

What is claimed is:

1. A process for the virtually complete isomerization of normal paraffin hydrocarbons contained in a feed stream consisting essentially of mixed normal and non-normal hydrocarbons comprising
   (a) passing a combined reactor feed of said feed stream and a desorption effluent, as hereinafter delineated, through an isomerization reactor containing an isomerization catalyst and including hydrogen in said reactor feed to convert at least a portion of the normal hydrocarbons in said reactor feed to non-normal hydrocarbons;
   (b) passing the reactor effluent from the reactor to an adsorption section and adsorbing the normal hydrocarbons remaining in the reactor effluent in a molecular sieve zeolite adsorber bed and passing the non-normal hydrocarbons out of the adsorption section as adsorber effluent containing an isomerate product;
   (c) desorbing the adsorber bed with an essentially constant hydrogen purge gas thereby producing a variable desorption vapor effluent comprised of a constant flow of hydrogen purge gas which contains a varying concentration of desorbed normal hydrocarbons in the range of 20 to 30 mole percent at the beginning of the desorption step to less than 5 mole percent at the end of such step; and
   (d) controllably varying the fresh feed stream flow rate and blending such fresh feed stream with the desorption effluent produced in step (c) to provide a constant flow of combined reactor feed in step (a).

2. A process according to claim 1 wherein the flow of the combined reactor feed is monitored by a flow control device, and the fresh feed flow rate is varied in response to variation in the flow rate of the combined feed flow rate, and monitoring the variation in fresh feed flow rate with a range control instrument which computes the average fresh feed flow rate, continuously compares the average fresh feed flow rate with a set point on the instrument and adjusts in response to such comparison the set point on the combined reactor feed flow control device which in turn controls the fresh feed flow rate to keep the combined reactor feed rate essentially constant.

3. A process according to claim 1 wherein the catalyst is a molecular sieve zeolite catalyst.

4. A process according to claim 1 wherein the adsorption section consists of a four bed system.

5. A process according to claim 4 wherein the adsorber effluent is heat exchanged with said feedstock to preheat such feedstock prior to controllably blending said feedstock with the desorption effluent.

* * * * *